United States Patent [19]

Post et al.

[11] Patent Number: 5,037,856

[45] Date of Patent: Aug. 6, 1991

[54] PROCESS FOR THE PREPARATION OF HYDROCARBONS FROM CO AND $H_2$

[75] Inventors: Martin F. M. Post, Amsterdam; Willibrord A. Van Erp, The Hague, both of Netherlands

[73] Assignee: Shell Oil Company, Houston, Tex.

[21] Appl. No.: 520,428

[22] Filed: May 8, 1990

[30] Foreign Application Priority Data

May 15, 1989 [GB] United Kingdom ................. 8911075

[51] Int. Cl.$^5$ ................................................ C07C 1/04
[52] U.S. Cl. ..................................... 518/714; 518/715
[58] Field of Search ................. 518/715, 714

[56] References Cited

FOREIGN PATENT DOCUMENTS 127220 12/1984 European Pat. Off. .
2161177A 1/1986 United Kingdom .
2169919 7/1986 United Kingdom ................. 518/715

Primary Examiner—Howard T. Mars

[57] ABSTRACT

The invention relates to a process for the preparation of hydrocarbons by catalytic reaction of carbon monoxide with hydrogen, comprising the steps of:

a) selecting a catalyst comprising:
  i) 3-80 parts by weight cobalt;
  ii) 0.1-100 parts by weight of at least one metal selected from zirconium, titanium and chromium, per 100 parts by weight silica, alumina and/or silica-alumina; and
  iii) an external surface area (Se)

$Se \leq 70 \text{ cm}^2/\text{ml}$;

b) activating the catalyst; and
c) contacting the activated catalyst in a fixed bed form with a mixture of carbon monoxide and hydrogen having a hydrogen/carbon monoxide feed ratio (F)

$F \leq 1.9$ under such conditions that $Se/F \geq 12.5$.

11 Claims, No Drawings

PROCESS FOR THE PREPARATION OF HYDROCARBONS FROM CO AND H$_2$

FIELD OF INVENTION

This invention relates to a process for the preparation of hydrocarbons by catalytic reaction of carbon monoxide with hydrogen.

BACKGROUND OF INVENTION

The preparation of hydrocarbons from an H$_2$/CO mixture by contacting this mixture at elevated temperature and pressure with a catalyst, is known in the literature as the Fischer-Tropsch hydrocarbon synthesis process. The products that can be prepared usually possess a very wide molecular weight distribution and in addition to branched and unbranched paraffins often contain considerable quantities of olefins and oxygen-containing organic compounds. As a rule only a minor portion of the resultant products consists of so-called middle distillates. "Middle distillates" refers to hydrocarbon mixtures having a boiling temperature range principally corresponding to that of the kerosine and gas oil fractions which are obtained in the conventional atmospheric temperature range distillation of crude petroleum. The middle distillate temperature range lies substantially between about 150° and 360° C. Besides the yield, the pour point of these middle distillates is not optimal. Accordingly, the direct conversion of H$_2$/CO mixtures by the Fischer-Tropsch process is not a particularly attractive route for the preparation of middle distillates on the technical scale.

The British patent 2,161,177 discloses a similar hydrocarbon synthesis process, using Fischer-Tropsch catalysts. The yield of middle distillates, expressed in terms of C$_5$+ selectivity, is improved if a catalyst having a specific texture is used, namely an external surface area of 5-70 cm$^2$/ml, an internal surface area (SI of 10-400 m$^2$/ml, under the provision that $10^6 > S_e^2 \times S_i > 2.5 \times 10^4$.

The C$_5$+ selectivity improvement is only disclosed for a hydrogen/carbon monoxide feed ratio (F) of 2.

DETAILED DESCRIPTION OF THE INVENTION

Recently a class of Fischer-Tropsch catalysts was discovered which posses the property of providing a product containing only very few olefins and oxygen-containing organic compounds and consisting virtually completely of unbranched paraffins a substantial proportion of which have a boiling point above the middle distillate range. It has been found that the high-boiling portion of this product can be converted at high yield into middle distillates by means of hydrocracking. The feedstock chosen for the hydrocracking treatment is at least that portion of the product of which the initial boiling point is above the final boiling point of the heaviest middle distillate desired as the end product. The hydrocracking treatment, which features a very low hydrogen consumption, yields middle distillates with a considerably better pour point than those obtained in the direct conversion of an H$_2$/CO mixture by the Fischer-Tropsch process.

The Fischer-Tropsch catalysts belonging to the above-mentioned class contain silica, alumina or silica-alumina as a carrier and cobalt together with zirconium, titanium and/or chromium as catalytically active metals in such proportions that the catalyst contain 3-80 parts by weight of cobalt and 0.1-100 parts by weight of zirconium, titanium and/or chromium per 100 parts by weight of carrier. The catalysts may by prepared by applying the metals to the carrier by means of kneading and/or impregnation. For further information concerning the preparation of these catalysts by kneading and/or impregnation reference is made to the European patent application 0.127,220 of Applicants all of the teachings of which are herein incorporated by reference.

It has now been found that the C$_5$+ selectivity of these cobalt promoted catalysts may be further improved if similar catalysts having a specific external catalyst surface area (S$_e$) are contacted in a fixed bed at a specific hydrogen/carbon monoxide feed ratio (F).

The present invention relates to a process for the preparation of hydrocarbons by catalytic reaction of carbon monoxide with hydrogen, comprising the steps of:

a) selecting a catalyst comprising:
  i) 3-80 parts by weight cobalt;
  ii) 0.1-100 parts by weight of at least one metal selected from zirconium, titanium and chromium, per 100 parts by weight silica, alumina, and/or silica-alumina; and
  iii) an external surface area (Se)

Se ≦ 70cm$^2$/ml;

b) activating the catalyst; and
c) contacting the activated catalyst in a fixed bed form with a mixture of carbon monoxide and hydrogen having a hydrogen/carbon monoxide feed ratio (F)

F ≦ 1.9 under such conditions that

Se/F ≧ 12.5

The external catalyst surface area S$_e$ may be determined for a representative sample of a given volume expressed in ml, by determining the external surface area expressed in cm$^2$ of each of the catalyst particles present therein, by summing the external surface areas found and by dividing the sum by the volume of the sample.

The cobalt promoted catalysts used in the process of the invention are preferably prepared by one of the following procedures:

a) cobalt is first applied by impregnation in one or more steps and subsequently the other metal is likewise applied by impregnation in one or more steps;

b) the other metal is first applied by impregnation in one or more steps and subsequently cobalt is likewise applied by impregnation in one or more steps;

c) cobalt is first applied by kneading in one or more steps and subsequently the other metal is applied by impregnation in one or more steps; or d) cobalt and the other metal are applied by kneading in one single step.

In the process according to the invention the cobalt promoted catalysts preferably contain 15-50 parts by weight cobalt per 100 parts by weight carrier. The quantity of other metals, when present, depends among other things on the manner in which these metals are applied. In the above procedure a) the catalysts finally contain 0.1-5 parts by weight of the other metals per 100 parts by weight carrier. In procedure b) the catalysts contain preferably from about 5 to 40 parts by weight of the other metals per 100 parts by weight carrier. It is preferred to use as the other metal zirconium and as the carrier silica.

It was surprising to find that the $C_5+$ selectively improved at a specific external catalyst surface area ($S_e$) lower than 70 cm$^2$/ml at feed ratios lower than 1.9, because as the feed ratio decreases, the occurrence of the so-called Boudouard-reaction increases, especially in the downstream part of the reactor, resulting in a conversion of carbon monoxide into carbon dioxide and carbon. The carbon will deposit on the catalyst, which deposition is detrimental to the catalyst activity. The hydrocarbon/carbon monoxide mixture feed used in the process according to the invention should have a hydrogen/carbon monoxide feed ratio less than 1.9 or at the most equal to 1.9. Preferably the feed ratio is less than 1.75, more preferably less than 1.5, still more preferably at a feed ratio of about 1.1-1.2.

Preferably the external surface area $S_e$ of the cobalt promoted catalyst is less than 50 cm$^2$/ml. The best results are obtained with a catalyst having an external surface area $S_e$ of about 20-50 cm$^2$/ml.

Mixtures of carbon monoxide and hydrogen, which are suitable for the process according to the invention might be obtained by subjecting light hydrocarbons, such as methane, to steam reforming or partial oxidation. Specific preference is given to the use of natural gas as feedstock.

The catalytic process according to the invention is normally carried out at a temperature of 125°-350° C., preferably at a reaction temperature of about 200°-250° C. The reaction pressure is normally 5 to 500 bar abs, preferably 15-30 bar abs.

Prior to use of the catalysts in the process according to the invention, the cobalt promoted catalysts have to be activated. This activation can suitably be carried out by contacting the catalysts at a temperature between 200° and 350° C. with hydrogen or a hydrogen containing gas.

Although in the preparation of middle distillates the product obtained over the cobalt catalyst may be used as such as feedstock it is sufficient to use as a feedstock for the hydrocracking treatment that portion of the product of which the initial boiling point is above the final boiling point of the heaviest middle distillate desired as end product. For this purpose it is preferred to use the total $C_5+$ fraction of the product prepared with the cobalt catalyst, because it has been found that under the influence of catalytic hydrogen treatment, a quality improvement takes place in the gasoline, kerosine and gas oil fractions present therein.

The hydrocracking treatment is carried out by contacting the fraction to be treated, at elevated temperature and pressure and in the presence of hydrogen, with a catalyst containing one or more noble metals of Group VIII on a carrier. The hydrocracking catalyst used is preferentially a catalyst containing 0.1-2% by weight and in particular 0.2-1% by weight of one or more noble metals of Group VIII on a carrier. Preference is given to catalysts containing as Group VIII noble metal platinum or palladium, and silica-alumina as carrier. The hydrocracking treatment is preferentially carried out at a temperature of 200°-400° C. and in particular of 275°-375° C. and a pressure of 5-200 bar and in particular of 10-75 bar.

The process according to the invention will be further illustrated with reference to the following example.

EXAMPLE

Ten Co/Zr/SiO$_2$ catalysts (catalysts 1-10) were prepared by impregnation of spherical silica carriers with solutions of cobalt and zirconium compounds. In each impregnation step a quantity of solution was used of which the volume substantially corresponded to the pore volume of the carrier concerned. After each impregnation step the solvent was removed by heating and the material was calcined at 500° C. After the final calcination the compositions were activated in hydrogen as follows: catalysts 1 and 4 at 250° C. and catalysts 2, 3 and 5-10 at 260° C. Catalysts 1-10 were prepared as follows.

CATALYSTS 1 AND 4

One-step impregnation of a silica carrier with an aqueous solution of cobalt nitrate, followed by one-step impregnation of the cobalt-loaded carrier with an aqueous solution of zirconium nitrate.

CATALYSTS 2, 3 AND 5-10

Two-step impregnation of a silica carrier with a solution of zirconium tetra-n-propoxide in a mixture of n-propanol, toluene and acetyl acetone, followed by one-step impregnation of the zirconium-loaded carrier with an aqueous solution of cobalt nitrate.

Further particulars of catalysts 1-10 are shown in the table. The catalysts 1-10 were used for the preparation of hydrocarbons from a mixture of carbon monoxide and hydrogen having H$_2$/CO molar ratios shown in the table.

The reactions with the various catalysts were carried out with a predetermined mixture of carbon monoxide and hydrogen, at such a temperature that the space time yield (C$_{1+}$ production [g/l/h]) is 100.

It is apparent from the table that the experiments carried out with the catalysts 1-7 and 9 are according to the invention and show a $C_5+$ selectivity of more than 80% by weight, whereas the experiments carried out with the catalysts 8 and 10 show a much lower $C_5+$ selectivity (72-78% by weight). Decisive for an improved $C_5+$ selectivity is the combination of a specific external catalyst surface area Se and a specific hydron-/carbon monoxide feed ratio F, the ratio of these values ($S_e$/F) should be larger or equal to 12.5, preferably larger than 20, most preferred lying within the range 20-40.

| CATALYST NO. | CATALYSTS AND EXPERIMENTAL CONDITIONS AND RESULTS | | | | | | | | | | |
| --- | --- | --- | --- | --- | --- | --- | --- | --- | --- | --- | --- |
|  | 1 | 2A | 2B | 3 | 4 | 5 | 6 | 7 | 8 | 9 | 10 |
| Zr load ppw Zr/100 ppw SiO$_2$ | 0.9 | 12 | 12 | 12 | 0.9 | 12 | 12 | 12 | 12 | 12 | 12 |
| Co load mg Co/ml catalyst | 83 | 102 | 102 | 96 | 90 | 101 | 105 | 102 | 100 | 96 | 101 |
| External Surface Area $S_e$ (cm$^2$/ml) | 24 | 23 | 23 | 24 | 22 | 21 | 40 | 20 | 20 | 16 | 14 |
| Temperature (°C.) | 217 | 210 | 218 | 220 | 225 | 218 | 210 | 225 | 212 | 230 | 225 |
| Pressure (bar abs) | 20 | 25 | 25 | 25 | 20 | 20 | 25 | 25 | 25 | 25 | 25 |

| CATALYST NO. | CATALYSTS AND EXPERIMENTAL CONDITIONS AND RESULTS | | | | | | | | | |
| --- | --- | --- | --- | --- | --- | --- | --- | --- | --- | --- |
| | 1 | 2A | 2B | 3 | 4 | 5 | 6 | 7 | 8 | 9 | 10 |
| Space Velocity of $H_2 + CO$ ($Nl.l^{-1}.h^{-1}$) | 600 | 600 | 750 | 600 | 600 | 600 | 750 | 600 | 600 | 600 | 750 |
| $H_2/CO$ ratio (F) | 1.8 | 1.8 | 1.5 | 1.1 | 1.5 | 1.5 | 1.1 | 1.1 | 1.8 | 1.1 | 1.8 |
| $H_2 + CO$ conversion (% v) | 84 | 85 | 72 | 84 | 83 | 84 | 70 | 83 | 85 | 84 | 68 |
| $C_{1+}$ production ($g.l^{-1}.h^{-1}$) | 101 | 104 | 108 | 102 | 100 | 102 | 106 | 100 | 103 | 101 | 106 |
| $C_{5+}$ selectivity (% w) | 81 | 84 | 86 | 90 | 81 | 82 | 90 | 87 | 78 | 81 | 72 |
| Se/F | 13.33 | 12.78 | 15.33 | 21.82 | 14.67 | 14.00 | 36.36 | 18.18 | 11.11 | 14.55 | 7.78 |

What we claim as our invention is:

1. A process for the preparation of middle distillate hydrocarbons by the catalytic reaction of carbon monoxide and hydrogen in a fixed bed at a temperature of 125°–350° C. and a pressure of about 15–30 bar abs with an activated catalyst comprising 3–80 parts by weight cobalt, 0.1–100 parts by weight of at least one metal selected from the group consisting of zirconium, titanium and chromium per 100 parts by weight of a catalyst carrier selected from the group consisting of silica, alumina and silica-alumina and having an external surface area (Se) $\leq 70$ cm$^2$/ml, wherein the feed ratio of hydrogen to carbon monoxide (F) is about 1.1–1.2 and wherein the ratio of Se/F is $\geq 12.5$, said activation comprising contacting said catalyst at a temperature between 200° and 350° C. with a hydrogen-containing gas or hydrogen.

2. The process of claim 1 wherein said external surface area (Se) is less than 50 cm$^2$/ml.

3. The process of claim 1 wherein said external surface area (Se) is about 20–50 cm$^2$/ml.

4. The process of claim 1 wherein Se/F is larger than 20.

5. The process of claim 1 wherein Se/F is about 20–40.

6. The process of claim 1 wherein the reaction temperature is about 200°–250° C.

7. In a process for the preparation of middle distillate hydrocarbons having a certain $H_2/CO$ feed ratio (F) at a temperature of 125°–350° C. and a pressure of 15–30 bar abs. by catalytically reacting $H_2$ and CO in a fixed bed in the presence of an activated catalyst comprising
   i) a carrier selected from the group consisting of silica, alumina and silica-alumina having an external surface area (Se) of $\leq 70$ cm$^2$/ml;
   ii) 3–80 parts by weight cobalt; and
   iii) 0.1–100 parts by weight of at least one metal selected from the group consisting of zirconium, titanium and chromium per 100 parts by weight of said selected silica, alumina and/or silica-alumina, the improvement consisting of keeping the $H_2/CO$ feed ratio F at about 1.1–1.2, and maintaining the Se/F at greater than or equal to 12.5.

8. The process of claim 7 wherein said external surface area (Se) is about 20–50 cm$^2$/ml.

9. The process of claim 7 wherein Se/F is larger than 20.

10. The process of claim 7 wherein Se/F is about 20–40.

11. The process of claim 7 wherein said catalyst is activated by contacting said catalyst at a temperature of 200° to 350° C. in the presence of a hydrogen-containing gas or hydrogen prior to contact of said catalyst with $H_2$ and CO.

* * * * *